(12) United States Patent
Kohn et al.

(10) Patent No.: US 8,591,951 B2
(45) Date of Patent: Nov. 26, 2013

(54) TRI-BLOCK COPOLYMERS FOR NANOSPHERE-BASED DRUG DELIVERY

(76) Inventors: Joachim B. Kohn, South Plainfield, NJ (US); David Devore, Princeton, NJ (US); Larisa Sheihet, Highland Park, NJ (US); Robert Dubin, Upper Montclair, NJ (US)

(*) Notice: Subject to any disclaimer, the term of this patent is extended or adjusted under 35 U.S.C. 154(b) by 642 days.

(21) Appl. No.: 11/191,181

(22) Filed: Jul. 27, 2005

(65) Prior Publication Data

US 2006/0013882 A1    Jan. 19, 2006

Related U.S. Application Data (63) Continuation-in-part of application No. 10/514,215, filed as application No. PCT/US03/15600 on May 15, 2003, now abandoned.

(60) Provisional application No. 60/378,042, filed on May 15, 2002.

(51) Int. Cl.
*A61K 9/14*     (2006.01)
*C08G 63/48*   (2006.01)

(52) U.S. Cl.
USPC .................................. 424/486; 525/54.1

(58) Field of Classification Search
USPC ....................................................... 424/425
See application file for complete search history.

(56) References Cited

U.S. PATENT DOCUMENTS

| | | | |
|---|---|---|---|
| 4,452,973 A * | 6/1984 | Casey et al. | 528/354 |
| 4,980,449 A | 12/1990 | Kohn et al. | |
| 5,099,060 A * | 3/1992 | Kohn et al. | 560/40 |
| 5,216,115 A | 6/1993 | Kohn et al. | |
| 5,587,507 A | 12/1996 | Kohn et al. | |
| 5,658,995 A * | 8/1997 | Kohn et al. | 525/432 |
| 5,670,602 A | 9/1997 | Kohn et al. | |
| 5,877,224 A * | 3/1999 | Brocchini et al. | 514/772.2 |
| 6,103,255 A | 8/2000 | Levene et al. | |
| 6,120,491 A | 9/2000 | Kohn et al. | |
| RE37,160 E * | 5/2001 | Kohn et al. | 560/40 |
| RE37,795 E * | 7/2002 | Kohn et al. | 528/176 |
| 6,475,577 B1 | 11/2002 | Hopton et al. | |
| 7,005,031 B2 * | 2/2006 | Lucast et al. | 156/330.9 |
| 7,271,234 B2 * | 9/2007 | Kohn et al. | 528/196 |
| 2006/0034769 A1 | 2/2006 | Kohn et al. | |
| 2006/0182752 A1 * | 8/2006 | Kohn et al. | 424/184.1 |

OTHER PUBLICATIONS

Mathiowitz et al., "Polyanhydride Microspheres as Drug Carriers. II. Microencapsulation by Solvent Removal," Journal of Applied Polymer Science, vol. 35, 755-774 (1988).*

Polansky, Dmitry E., Novel Radical Peroxyester Photoinitiators: Decompositio Mechanisms and Potential Applications, Graduate College of Bowling Green State University, Dec. 2005, pp. 1 and 4-5.*

(Continued)

*Primary Examiner* — Ernst Arnold
*Assistant Examiner* — Jianfeng Song
(74) *Attorney, Agent, or Firm* — Fox Rothschild LLP (57) ABSTRACT

Biocompatible non-toxic triblock copolymers having an A-B-A structure wherein each A is a hydrophilic, biocompatible end block and the B middle block is a hydrophobic desaminotyrosyl tyrosine polycarbonate or polyarylate. The copolymers spontaneously self-assemble to form low critical aggregation concentration nanospheres having utility as delivery vehicles for hydrophobic biologically or pharmaceutically active compounds.

15 Claims, 7 Drawing Sheets

Structure of PEG-*b*- oligo(DTR-SA)-*b*-PEG triblock copolymers

DTE: R= Ethyl     DTB: R= n-Butyl     DTBn: R= Benzyl     DTO: R= n-Octyl

(56) References Cited

OTHER PUBLICATIONS

Alexandridis, P., Amphiphilic copolymers and their applications, Curr. Opin. Colloid Interface Sci., 1996, vol. 1(4), pp. 490-501.

Aranda-Espinoza, H., et al., Electromechanical Limits of Polymersomes, Phys. Rev. Lett., 2001, vol. 87, No. 20, 208301-1-208301-4.

Bourke, S. L.; Kohn, J., Polymers derived from the amino acid L-tyrosine: polycarbonates, polyarylates and copolymers with poly-(ethylene glycol), Adv. Drug Del. Rev., 2003, vol. 55, (4), pp. 447-466.

Bronich, T. K., et al., Recognition of DNA Topology in Reactions between Plasmid DNA and Cationic Copolymers, J. Am. Chem. Soc. 2000, vol. 122, No. 135, pp. 8339-8343.

Burke, S. E.; Eisenberg, A., Kinetic and Mechanistic Details of the Vesicle-to-rod Transition in Aggregates of PS310-b-PAA52 in Dioxam-water Mixtures, Polymer 2001, vol. 42, pp. 9111-9120.

De Jaeghere, F., et al., Cellular uptake of PEO Surface-modified Nanoparticles: Evaluation of Nanoparticles made of PLA: PEO diblock and triblock copolymers, J. Drug Target. 2000, vol. 8 (3), pp. 143-153.

Discher, B. M., et al., Polymersomes: Tough Vesicles Made from Diblock Copolymers, Science, May 14, 1999, vol. 284, pp. 1143-1146.

Greenwald, R. B., et al., Effective Drug Delivery by PEGylated Drug Conjugates, Adv. Drug Delivery Rev., 2003, vol. 55, pp. 217-250.

Haag, R., Supramolecular Drug-Delivery Systems Based on Polymeric Core-Shell Architectures, Angew Chem. Int. Ed. Engl., 2004, 43, pp. 278-282.

Hoffman, A. S., et al., Design of "Smart" Polymers that Can Direct Intracellular Drug Delivery, Polym. Adv. Technol. 2002, 13, pp. 992-999.

Jagur-Grodzinski, J. Biomedical Applications of Polymers 2001-2002, e-Polymers, 2003, No. 12, pp. 1-38.

Jung, S. W., et al, Characterization of Hydrophobized Pullulan with Various Hydrophobicities, Int. J. Pharm., 2003, 254, pp. 109-121.

Kemnitzer, J.; Kohn, J., Degradable polymers derived from the amino acid L-tyrosine. In Handbook of Biodegradable Polymers, Domb, A. J.; Kost, J.; Wiseman, D. M., Eds. Harwood Academic Publishers: Amsterdam, The Netherlands, 1997; vol. 7, pp. 251-272.

Lynn, D. M., et al., Accelerated Discovery of Synthetic Transfection Vectors: Parallel Synthesis and Screening of a Degradable Polymer Library, J. Am. Chem. Soc., 2001, 123, pp. 8155-8156.

Nardin, C; Bolikal, D.; Kohn, Nontoxic Block Copolymer Nanospheres: Design and Characterization, Langmuir, 2004, 20, pp. 11721-11725.

Nardin, C.; Meier, W., Hybrid Materials from Amphiphilic Block Copolymers and Membrane Proteins, Rev. Mol. Biotech., 2002, 90, pp. 17-26.

Soppimath, K. S., et al., Biodegradable Polymeric Nanoparticles as Drug Delivery Devices, J. Contr. Rel., 2001, 70, pp. 1-20.

Vila, A. et al., PLA-PEG Nanospheres: New Carriers for Transmucosal Delivery of Proteins and Plasmid DNA, Polym. Adv. Technol., 2002, 13, pp. 851-858.

Benzina et al., A versatile three-iodine molecular building block leading to new radiopaque polymeric biomaterials, Journal of Biomedical Materials Research, Nov. 1, 1996, pp. 459-466, vol. 32, John Wiley & Sons, Inc., US.

* cited by examiner

Figure 1. Structure of PEG-*b*- oligo(DTR-SA)-*b*-PEG triblock copolymers

| DTE: R= Ethyl | DTB: R= n-Butyl | DTBn: R= Benzyl | DTO: R= n-Octyl |

Figure 2. Molecular weight propoerties of the PEG-*b*-oligo(DTR-SA)-*b*-PEG triblock copolymers and their corresponding nanosphere hydrodynamic diameters

| Polymers/ Nanospheres | Oligo (DTR-SA) block Mn | Oligo (DTR-SA) block Mw | Triblock Mn | Triblock Mw | Triblock Polydispersity (Mw/Mn) | Nanosphere Hydrodynamic diameter, nm |
|---|---|---|---|---|---|---|
| 2K/DTE-SA | 6,400 | 11,300 | 10,800 | 21,000 | 1.94 | 44.0 ± 23.6 |
| 5K/DTE-SA | 6,100 | 11,200 | 15,200 | 25,100 | 1.65 | 67.3 ± 32.2 |
| 2K/DTB-SA | 6,000 | 11,700 | 10,300 | 19,800 | 1.92 | 44.8 ± 18.3 |
| 5K/DTB-SA | 6,100 | 11,800 | 15,400 | 25,300 | 1.64 | 70.8 ± 30.3 |
| 2K/DTBn-SA | 6,300 | 13,600 | 10,800 | 21,500 | 1.99 | 47.2 ± 16.0 |
| 5K/DTBn-SA | 6,400 | 13,300 | 15,700 | 25,000 | 1.59 | 68.0 ± 30.9 |
| 2K/DTO-SA | 6,800 | 13,000 | 11,500 | 20,200 | 1.76 | 47.5 ± 30.9 |
| 5K/DTO-SA | 6,100 | 12,600 | 15,500 | 25,000 | 1.61 | 73.6 ± 31.5 |

Figure 3. Thermal behavior of oligo(DTR-SA) blocks and PEG-*b*-oligo(DTR-SA)-*b*-PEG triblock copolymers

| Oligomer | Tg °C | Triblock copolymer | Tg °C | Tm °C |
|---|---|---|---|---|
| DTB-SA | 42 | 2K/DTB-SA | -33 | 47 |
|  |  | 5K/DTB-SA | -34 | 52 |
| DTO-SA | 21 | 2K/DTO-SA | -32 | 49 |
|  |  | 5K/DTO-SA | -34 | 54 |

Figure 4. Nanosphere-model compound interaction

Figure 5. Analysis of fractions following gel filtration chromatography

Figure 6. Non-toxic behavior of nanospheres

Figure 7. Paclitaxel's anti-tumor cell activity co-migrates with the nanospheres

TRI-BLOCK COPOLYMERS FOR NANOSPHERE-BASED DRUG DELIVERY

CROSS-REFERENCE TO RELATED APPLICATIONS

The present application is a continuation-in-part of U.S. patent application Ser. No. 10/514,215 filed Nov. 10, 2004, which claims priority benefit under 35 U.S.C. §371 of PCT Application No. PCT/US03/015600 filed on May 15, 2003; which, in turn, claims priority benefit under 35 U.S.C. §119 (e) of U.S. Provisional Patent Application No. 60/378,042 filed May 15, 2002. The disclosures of all three applications are incorporated herein by reference.

BACKGROUND OF THE INVENTION

An important issue facing the pharmaceutical and biotechnology industries is the limited availability of effective, non-toxic delivery systems for hydrophobic therapeutic compounds. For example, paclitaxel, the treatment of choice for tumors of the breast and ovary, is hydrophobic. Therefore, clinical administration of paclitaxel requires dispersion in an oil and ethanol excipient that has been linked to unwanted side effects.

Synthetic polymers have shown advantages as delivery vehicles for many pharmacological materials, providing increased solubility and stability of bound therapeutic compounds and the opportunity for targeted delivery to a restricted population of cells. Nanospheres, i.e., carriers with a size in the submicron range, are desirable for intravascular administration. For this purpose, the recent advances in supramolecular chemistry allow designing materials of superior characteristics.

For parenteral delivery systems, it has been shown that nano-sized particles and liposomes have great potential in cancer therapy due to their ability to extravasate from the leaky vasculature of tumors. To achieve this objective, various nano-sized particles or colloidal carriers such as nanospheres, polymeric micelles, liposomes, and surface modified nanoparticles have been proposed. However, the distribution of drugs and carriers in the body, undesirable side effects, rapid clearance by macrophage, thermal instability, structural fragility and low drug loading efficiency, among other factors, have limited these approaches and only a few such delivery systems have progressed toward clinical use.

For liposomal systems, their poor shelf stability and insufficient loading has been a substantial barrier. A number of polymeric systems have been investigated, with PLGA [poly (D,L-lactide-co-glycolide)] and PLA-PEG [poly(D,L-lactic acid)-poly(ethylene glycol)] being the most widely studied because they are biodegradable, of low antigenicity, and approved for drug use but their reported drug incorporation levels have been generally quite low, thus making it difficult to encapsulate sufficient drug for therapeutic efficacy. Improved drug incorporation has been seen using cyanoacrylate polymers, but these systems show some toxicity. Another disadvantage of many of the nanoparticles produced using the nanoprecipitation/solvent extraction technique is the need for a surfactant during nanoparticle formation. Sufficient removal of the surfactant and/or residual solvent is always a problem.

Of particular interest are nanoparticles formed via the self-assembly of block copolymers. Similar to low molecular weight lipid or surfactant molecules, amphiphilic block copolymers consist of at least two parts, a hydrophilic block and a hydrophobic block. Such amphiphilic block copolymers, driven by their hydrophobicity, can self-assemble in aqueous solution. At high concentrations, they may build lamellar liquid crystalline phases whereas, in dilute aqueous solution, they may form superstructures of various shapes like micelles or vesicular structures.

A suitable neutral amphiphilic block copolymer forms spontaneously nanometer-sized, well-defined hollow sphere structures in dilute aqueous solution. These structures can be viewed as the high molecular weight analogues of lipid or surfactant molecules. However due to their slow dynamic, they form much more stable superstructures than conventional liposomes. Furthermore, liposomes, e.g., spherically closed lipid bilayers, are rapidly recognized by the immune system and cleared from the blood stream. Due to the wide variety of block copolymer chemistry one can prepare an entirely synthetic material to avoid immunogenic reactions.

Although it is well known that suitable block copolymers can form nanospheres, few were designed to self-assemble into biocompatible and biodegradable structures in dilute aqueous solution. One example of spontaneous aggregation of an amphiphilic block oligomer has been reported with a poly(methyloxazoline)-block-poly(dimethyl-siloxane)-block-poly (methyl-oxazoline), PMOXA-PDMS-PMOXA triblock oligomer. Injection combined with extrusion techniques leads to the formation of vesicles whose size can be controlled between 50 and 500 nm. However, there remains a need for non-cytotoxic, biodegradable triblock copolymer vesicles.

Block copolymer vesicles are of interest for drug delivery applications for a number of reasons. First of all, hydrophobic drugs can be physically entrapped in the core of block copolymer micelles and transported at concentrations that can exceed their intrinsic water-solubility. Secondly, the hydrophilic blocks, which are often composed of poly(ethylene oxide) (PEO), can form hydrogen bonds with the aqueous surroundings and form a tight shell around the micellar core. As a result, the contents of the hydrophobic core are effectively protected against hydrolysis and enzymatic degradation. In addition, the PEO corona prevents recognition by the reticuloendothelial system and therefore preliminary elimination of the micelles from the bloodstream.

Consequently, the use of polymeric nanoparticles for the advantages of stability, cost, and ease of formulation is more preferable. It is expected, that drug incorporation and control of drug release, could be altered by the introduction of moieties into the polymers, which could increase the level of interaction with the drug. This strategy requires biodegradable polymers to enable in vivo biodegradation and subsequent removal from the body.

SUMMARY OF THE INVENTION

Our approach has been to develop a versatile copolymeric architecture for nanospheres that can deliver a wide array of hydrophobic therapeutic agents. We further demonstrate here that the nanospheres strongly complex hydrophobic molecules such as the anti-tumor agent, paclitaxel, and effectively deliver them to tumor cells in vitro.

A family of ABA-type triblock copolymers that self-assembles into nanospheres has now demonstrated the ability to complex important hydrophobic compounds. These copolymers spontaneously self-assemble in aqueous solutions into nanospheres whose properties are shown to be a function of several independent and readily controlled synthetic variations, including the molecular weights of the A- and B-blocks, and the molecular composition of the pendent ester R groups.

The triblock copolymers are derived from water-soluble, hydrophilic, and non-toxic end blocks and a hydrophobic middle block of either a polyarylate or polycarbonate. Thus, according to one specific aspect of the present invention, a triblock copolymer having an A-B-A structure wherein each A end block is water-soluble, hydrophilic, and non-toxic; and the B middle block is a polycarbonate with the same or different repeating units having the structure according to Formula (I):

wherein X is

Z is between 2 and about 100, inclusive; $R_1$ is CH=CH or $(CH_2)_n$ wherein n is from 0 to 18, inclusive; and $R_2$ is selected from the group consisting of hydrogen and straight and branched alkyl and alkylaryl groups containing up to 18 carbon atoms.

The triblock copolymers self-assemble spontaneously to form biocompatible, biodegradable nanospheres, which are useful for the delivery of drugs and other actives even at very low concentration.

Therefore, according to another aspect of the present invention, a composition is provided comprising (a) nanospheres of a triblock copolymer having an A-B-A structure wherein each A end block is water-soluble, hydrophilic, and non-toxic; and the hydrophobic middle B block is hydrophobic with the same or different repeating units having the structure according to Formula (II):

wherein X is

Z is between 2 and about 100, inclusive; $R_1$ is CH=CH or $(CH_2)_n$ wherein n is from 0 to 18, inclusive; $R_2$ is selected from the group consisting of hydrogen and straight and branched alkyl and alkylaryl groups containing up to 18 carbon atoms; and R is selected from the group consisting of a bond or straight and branched alkyl and alkylaryl groups containing up to 18 carbon atoms; and (b) a hydrophobic compound complexed by said nanospheres.

The endblocks are preferably poly(alkylene oxides) having the structure of:

wherein m for each A is independently selected to provide a molecular weight for each A between about 1000 and about 15,000 g/mol; $R_3$ for each A and within each A is independently selected from hydrogen and lower alkyl groups containing from one to four carbon atoms; and a is an integer greater than or equal to one. In a preferred embodiment, the end blocks have the structure $CH_3O-[CH_2CH_2O-]_m$.

In particular, the copolymer nanospheres of the present invention can be used to complex drugs or other active ingredients such as anti-tumor agents, antibiotics, antimicrobials, statins, peptides, proteins, hormones, vaccines, and contrast agents, i.e., essentially any useful pharmaceutical or biological agent in the broadest sense, and provide a means for the prolonged release of the complexed materials. Therefore, according to yet another aspect of the present invention, compositions for delivering a hydrophobic active agent to a patient in need thereof are provided containing a pharmaceutically acceptable carrier and an effective amount of nanospheres complexing a hydrophobic agent with the triblock copolymer of the present invention.

Preferred embodiments of this aspect of the invention provide nanosphere-complexed biologically or pharmaceutically active compounds, wherein the active compound nanospheres are present in an amount sufficient for effective site-specific or systemic delivery. The carrier may be an aqueous solution in which the nanospheres are suspended, or a drug delivery matrix. This aspect of the present invention includes embodiments in which the copolymer nanospheres of the present invention function as a reservoir for active agents within a matrix-based, controlled release device (such as a hydrogel or any of the other types of controlled release systems as described in P. Sinko and J. Kohn, "Polymeric drug delivery systems: An overview", in: *Polymeric Delivery Systems: Properties and Applications*, (M. A. El-Nokaly, D. M. Piatt and B. A. Charpentier, eds.), ACS Symposium Series, Vol. 520, 1993, American Chemical Society, Washington, DC, 18-41).

Given this utility of the copolymer nanospheres of the present invention, according to still yet another aspect of the present invention, methods are provided for site-specific or systemic delivery by administering to a patient in need thereof an effective amount of a hydrophobic active compound complexed by the polymer nanospheres of the present invention.

The present invention represents a significant technological advance that has broad utility in the field of drug delivery and the controlled (or prolonged) release of active agents. Specifically, the family of triblock copolymers described herein has at least three major, distinguishing advantages over other triblock copolymers:

1. The family of triblock copolymers is fully resorbable after being introduced into a patient. As the compositions are derived exclusively of non-toxic building blocks, the triblock copolymers themselves as well as the expected degradation products in vivo are non-cytotoxic and biocompatible.

2. The family of triblock copolymers self-assemble to form nanospheres with a low critical aggregation concentration (CAC) and remain stable even under very high dilution.

3. The family of triblock copolymers provides a wide range of structural parameters which can be changed by those skilled in organic synthesis that are closely related to each other in overall chemical structure while allowing the tailoring of key properties (such as the rate of bioresorption, the physical characteristics of the nanospheres formed, and the release profiles obtained for encapsulated actives).

A more complete appreciation of the invention and many other intended advantages can be readily obtained by reference to the following Detailed Description of the Preferred Embodiments and claims, which disclose the principles of the invention and the best modes which are presently contemplated for carrying them out.

BRIEF DESCRIPTION OF THE DRAWINGS

FIGS. 5A-D represent an analysis of fractions of fluorescein-5K/DTO-SA and DAF-5K/DTO-SA nanospheres following gel filtration chromatography as follows:

DETAILED DESCRIPTION OF THE PREFERRED EMBODIMENTS

The copolymers of the present invention are A-B-A type triblocks. The A end blocks are water-soluble, hydrophilic, and non-toxic, preferably selected from poly(alkylene oxides), and the hydrophobic middle B block is either a polyarylate or polycarbonate. In a preferred polyarylate embodiment, the mid-block is copolymerized from a tyrosine-derived diphenol and a diacid, linked together by an ester bond between the phenolic hydroxyl group of the tyrosine-derived diphenol and the carboxylic acid group of the diacid. In another preferred embodiment, the polycarbonate mid-block is copolymerized from the same dihydroxy monomers.

Among the more preferred poly(alkylene oxides) end blocks are polyethylene glycol, polypropylene glycol, polybutylene glycol, Pluronic™ polymers, and the like. Polyethylene glycols are preferred.

The polyarylate middle blocks of the present invention are prepared by condensation of a diacid with a diphenol according to the method described by U.S. Pat. No. 5,216,115 in which diphenol compounds are reacted with aliphatic or aromatic dicarboxylic acids in a carbodiimide mediated direct polyesterification using 4-(dimethyl-amino)-pyridinium-p-toluene sulfonate (DPTS) as a catalyst. The disclosure of U.S. Pat. No. 5,216,115 in this regard is incorporated herein by reference. Bis-diacids are selected as the polyarylate middle blocks to permit the A end blocks to be coupled at each end of the copolymer.

The diphenol compounds are the tyrosine-derived diphenol monomers of U.S. Pat. Nos. 5,587,507 and 5,670,602, the disclosures of both of which are also incorporated herein by reference. The polyarylates are prepared using tyrosine-derived diphenol monomers having the structure of Formula III:

(III)

wherein $R_1$ and $R_2$ are the same as described above with respect to Formula II.

The preferred diphenol monomers are desaminotyrosyl-tyrosine carboxylic acids and esters thereof, wherein $R_1$ is —$CH_2$—$CH_2$—, which are referred to as DT esters. For purposes of the present invention, the ethyl ester ($R_2$=ethyl) is referred to as DTE, the benzyl ester ($R_2$=benzyl) as DTBn, and so forth. Both patents disclose methods by which these monomers may be prepared. For purposes of the present invention, the desaminotyrosyl-tyrosine free carboxylic acid ($R_2$=hydrogen) is referred to as DT.

The polyarylate dicarboxylic acids have the structure:

wherein R is the same as described above with respect to Formula II, and preferably contains up to 12 carbon atoms. R is preferably selected so that the dicarboxylic acids employed as starting materials are either important naturally-occurring metabolites or highly biocompatible compounds. Preferred Formula IV dicarboxylic acids therefore include the intermediate dicarboxylic acids of the cellular respiration pathway known as the Krebs cycle. These dicarboxylic acids include alpha-ketoglutaric acid, succinic acid, fumeric acid, malic acid, and oxaloacetic acid, for which R is —$CH_2$—$CH_2$—C(=O)—, —$CH_2$—$CH_2$—, —CH=CH—, —$CH_2$—CH(—OH)— and —$CH_2$—C(=O)—, respectively.

Another naturally-occurring, preferred dicarboxylic acid is adipic acid (R=(—$CH_2$—)$_4$), found in beet juice. Other preferred biocompatible dicarboxylic acids include oxalic acid (no R), malonic acid (R=—CH$_2$—), glutaric acid (R=(CH$_2$—)$_3$, pimellic acid (R=(—CH$_2$—)$_5$), suberic acid (R=(—CH$_2$—)$_6$) and azalaic acid (R=(—CH$_2$—)$_7$). In other words, among the dicarboxylic acids suitable for use in the present invention are compounds in which R represents (—CH$_2$—)$_z$ wherein z is an integer between 0 and 12, inclusive. A preferred class of highly biocompatible aromatic dicarboxylic acids are the bis(p-carboxyphenoxy) alkanes such as bis(p-carboxyphenoxy) propane.

The polyarylate triblock oligomers are synthesized in a one pot reaction using in situ carbodiimide coupling of a non-functionalized poly(alkylene oxide) monoalkyl ether and oligo (DTO suberate). The following is a specific example of this general design, illustrating the synthesis of PEG-oligo-(DTO suberate)-PEG:

The polycarbonate middle blocks of the present invention can be prepared by the conventional methods for polymerizing diphenols into the same, as described by U.S. Pat. No. 5,099,060 the disclosure of which is incorporated herein by reference. These methods involve the reaction of amino acid-derived diphenol compounds, including those described in U.S. Pat. No. 4,980,449, the disclosure of which is incorporated herein by reference, with phosgene or phosgene precursors (e.g. diphosgene or triphosgene) in the presence of a catalyst. Suitable processes, associated catalysts, and solvents are known in the art and are taught in Schnell, *Chemistry and Physics of Polycarbonates* (Interscience, New York 1964), the teachings of which are incorporated herein by reference.

It is not possible to polymerize oligomers having pendant free carboxylic acid groups from diphenols with pendant free carboxylic acid groups without cross-reaction of the free carboxylic acid groups with the co-monomer. Accordingly, homopolymers or copolymers of benzyl ester diphenyl monomers such as DTBn may be converted to corresponding free carboxylic acid homopolymers and copolymers through the selective removal of the benzyl groups by the palladium catalyzed hydrogenolysis method disclosed by co-pending and commonly owned U.S. Pat. No. 6,120,491. The disclosure of this patent is incorporated by reference. The catalytic hydrogenolysis is necessary because the lability of the oligomer backbone prevents the employment of harsher hydrolysis techniques. Another method, disclosed by co-pending and commonly owned U.S. patent application Ser. No. 10/952, 202, involves the selective removal of tert-butyl ester groups from a hydrolytically unstable polymer to form a new polymer composition having free carboxylic acid groups in place of the tert-butyl ester groups. The disclosure of this application is also incorporated by reference.

The triblock copolymers of the present invention may be iodine- and bromine-substituted, which renders the copolymers radio-opaque. These copolymers and their methods of preparation are disclosed by U.S. Pat. No. 6,475,577. The disclosure of this patent is incorporated herein by reference. Radio-opaque copolymers include repeating structural units in which one or more hydrogens of an aromatic ring, an alkylene carbon, or both, are replaced with an iodine or bromine atom. The triblock copolymers of the present invention may be similarly iodine- and bromine-substituted. Copolymers according to the present invention comprising the repeating structural units of Formula I are radio-opaque when copolymerized with radio-opaque monomers so that the copolymers also contain radio-opaque repeating structural units, preferably one or more of the A or B blocks in which one or more hydrogens of an aromatic ring, an alkylene carbon, or both, have been replaced with an iodine or bromine atom.

The molecular weights of the triblock copolymers can be controlled either by limiting the reaction time or the ratios of the components. Molecular weights can also be controlled by the quantity of the carbodiimide coupling reagent that is used.

Preferred polyarylates have weight average molecular weights between about 1,000 and 100,000 g/mol, preferably between about 3,000 and 50,000 g/mol, and more preferably between about 10,000 and 25,000 g/mol. Molecular weights are calculated by gel permeation chromatography relative to polystyrene standards in tetrahydrofuran without further correction. The triblock copolymers thus have weight average molecular weights between about 2,500 and 130,000 g/mol, preferably between about 5,000 and 80,000 g/mol, and more preferably between about 10,000 and 50,000 g/mol.

Preferred polycarbonates in accordance with the present invention have weight-average molecular weights ranging between about 1,000 and 100,000 g/mol, preferably between about 3,000 and 50,000 g/mol, and more preferably between about 10,000 and 25,000 g/mol. Molecular weights are calculated by gel permeation chromatography relative to polystyrene standards in tetrahydrofuran without further correction. The triblock copolymers thus have weight average molecular weights between about 2,500 and 130,000 g/mol, preferably between about 5,000 and 80,000 g/mol, and more preferably between about 10,000 and 50,000 g/mol.

The triblock copolymers degrade by hydrolysis into the original starting materials, i.e., the tyrosine-derived diphenols, the dicarboxylic acids, and the water-soluble, hydrophilic, and non-toxic oligomer end blocks. The inventive copolymers are highly hydrophilic, which is advantageous for nanosphere drug delivery systems. However, the hydrophilic:hydrophobic balance of the copolymers can be varied in several ways. The ester of the pendant chain of the diphenol can be changed, with longer-chain ester groups increasing hydrophobicity. Increasing the molecular weight of the A end blocks, for example, by increasing the number of carbons in the alkylene group of a poly(alkylene oxide) will also increase hydrophobicity. Changing the dicarboxylic acid will also change the hydrophilic:hydrophobic balance.

The triblock copolymers of the present invention form vesicular structures in dilute aqueous solutions in the 5-200 nm range (diameter). Preferred structures have diameters between 50 and 150 nm. For example, poly(ethylene glycol)-block-oligo-(DTO suberate)-block-poly(ethylene glycol), i.e., PEG-oligo-(DTO suberate)-PEG triblock oligomer, forms vesicular structures in dilute aqueous solution having a diameter of about 100 nm range. The vesicles are characterized with conventional techniques, i.e., light scattering.

The triblock copolymers thus can be used to form nanosphere hydrophobic drug delivery systems. The synthesis of a triblock copolymers comprised of non-cytotoxic and biodegradable building blocks and capable of forming nanospheres by a self-assembly process is important for use in many biomedical applications including but not limited to the use as a carrier for hydrophobic drugs. For purposes of the present invention, a hydrophobic active agent is defined as an active agent, such as a drug or other biologically active material, having a log P>0 relative to octanol, wherein P is the partition coefficient.

It is well established that the self-assembly of amphiphilic molecules depends on several correlated properties of the underlying material, i.e., its chemical structure, architecture or molecular weight. However, assuming that the driving force of the self-assembly is mainly governed by hydrophobic interactions, the design of a self-assembling block copolymer inherently depends on its molecular weight and hydrophobic to hydrophilic balance. The self-assembly of the triblock copolymers in dilute aqueous solution is induced by simple dropwise addition and may be facilitated by sonication, high shear mixing, nanoprecipitation or emulsification methods. Active hydrophobic products are complexed by premixing the triblocks and hydrophobic products in suitable solvent prior to nanosphere formation or by forming the nanospheres in solutions or suspensions of the product to be complexed.

The present invention therefore also includes injectable delivery systems for biologically and pharmaceutically active compounds formed by complexing the active compound with the nanospheres in a solution suitable for injection. The delivery system and its method of preparation are particularly well suited for use with active compounds such as pharmacologically active proteins, peptides, vaccines, and the like, as well as with other small pharmacologically active molecules and contrast agents. Specific active compounds include paclitaxel, camptothecin, 9-nitrocamptothecin, cisplatin, carboplatin, ciprofloxacin, doxorubicin, rolipram, simvastatin, methotrexate, indomethacin, probipprofen, ketoprofen, iroxicam, diclofenac, cyclosporine, etraconazole, rapamycin, nocodazole, colchicine, ketoconazole, tetracycline, minocycline, doxycycline, ofloxacin, gentamicin, octreotide, calcitonin, interferon, testosterone, progesterone, estradiol, estrogen, and insulin.

Nanospheres encapsulating a hydrophobic agent to be delivered may also be dispersed as a reservoir of the agent within the oligomeric matrix of controlled release device. The host oligomeric matrix may be a hydrogel or other bioerodible oligomer. Such dispersions would have utility, for example, as active agent depots in transdermal drug delivery devices.

The delivery systems of the present invention are suitable for applications where localized delivery is desired, as well as in situations where systemic delivery is desired. Therapeutically effective dosages may be determined by either in vivo or in vitro methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each active compound by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate of the active compound from the formulations of this invention are also varied within the routine skill in the art to determine an advantageous profile, depending on the therapeutic conditions to be treated.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

The compositions may be administered subcutaneously, intramuscularly, colonically, rectally, nasally, orally or intraperitoneally, employing a variety of dosage forms such as suppositories, implanted pellets or small cylinders, aerosols, oral dosage formulations and topical formulations, such as ointments, drops and transdermal patches. The dosage forms may optionally include one or more carriers.

Acceptable pharmaceutical carriers for therapeutic use are well known in the pharmaceutical field, and are described, for example, in *Remington's Pharmaceutical Science*, Mac Publishing Co., (A. R. Gennaro edt. 1985). Such materials are non-toxic to recipients at the dosages and concentrations employed, and include diluents, solubilizers, lubricants, suspending agents, encapsulating materials, solvents, thickeners, dispersants, buffers such as phosphate, citrate, acetate and other organic acid salts, anti-oxidants such as ascorbic acid, preservatives, low molecular weight (less than about 10 residues) peptides such as polyarginine, proteins such as serum albumin, gelatin or immunoglobulins, hydrophilic polymers such as poly(vinylpyrrolindinone), amino acids such as glycine, glutamic acid, aspartic acid or arginine, monosaccharides, disaccharides, and other carbohydrates including cellulose or its derivatives, glucose, mannose or dextrines, chelating agents such as EDTA, sugar alcohols such as mannitol or sorbitol, counter-ions such as sodium and/or non-ionic surfactants such as Tween™, Pluronics™, or PEG.

The nanosphere-drug complexes of this invention may be prepared for storage under conditions suitable for the preservation of drug activity as well as maintaining the integrity of the copolymers, including lyophilization, and are typically suitable for storage at ambient or refrigerated temperatures. Sterility may be readily accomplished by conventional methods.

The following non-limiting examples set forth hereinbelow illustrate certain aspects of the invention. All parts and percentages are by weight unless otherwise noted and all temperatures are in degrees Celsius. Dicarboxylic acids and all other reagents were purchased in pure form and were used as received. Solvents were of "HPLC grade." Diphenolic monomers (e.g., the esters of desamino tyrosil-tyrosine) were prepared according to the procedure provided in Example I of U.S. Pat. No. 5,099,060. Although this procedure refers specifically to DTH, monomers having esters other than the hexyl ester can be readily prepared by the same basic procedure. The DPTS catalyst was prepared as described by Moore, et al., *Macromol.*, 23 (1), 65-70 (1990).

EXAMPLES

Examples 1-2

Figure 1:
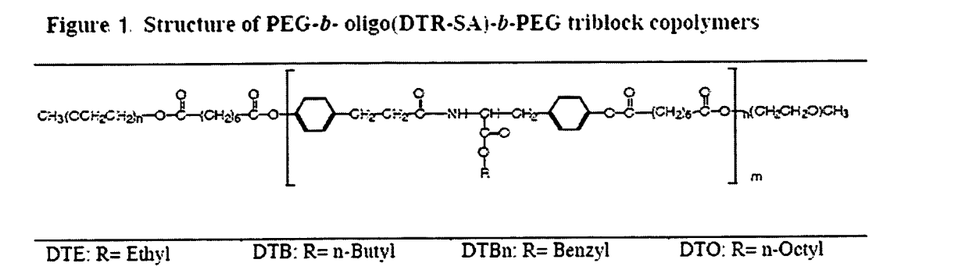
FIG. 1 is a representation of the structure of PEG-b-oligo (DTR-SA)-b-PEG triblock copolymers.

Preparation of poly(ethylene glycol)-block-oligo-(DTR suberate)-block-poly(ethylene glycol) Self-Assembling Nanospheres Nomenclature: The family of ABA triblock copolymers, poly(ethylene glycol)-block-oligo-(DTR suberate)-block-poly(ethylene glycol), are abbreviated as follows: the symmetrical PEG A-blocks are abbreviated as either 2K or 5K, meaning they have a molecular weight of 2000 or 5000 g/mol, respectively; the oligo B-blocks (suberic acid ester (SA) of desaminotyrosyl tyrosine alkyl ester (DTR)) are distinguished by their pendent ester R groups, where R is E=ethyl, B=n-butyl, B=n-octyl, or Bn=benzyl (FIG. 1). For example, the triblock oligomer PEG5K-b-oligo(desaminotyrosyl-tyrosine ethyl ester suberate)-b-PEG5K is abbreviated as 5K/DTE-SA.

Chemicals: Desaminotyrosyl tyrosine octyl ester (DTO) was prepared using known procedures. Methylene chloride (HPLC grade), 2-propanol, and methanol were obtained from Fisher Scientific, Pittsburgh, Pa. Suberic acid, 4-dimethylaminopyridinium-p-toluene sulfate (DMPTS), poly(ethylene glycol) monomethyl ether (Mw of 2000 or 5000 g/mol), and cetyltrimethylammonium bromide (CTAB) were obtained from Aldrich Chemical Co, Milwaukee, Wis. Diisopropylcarbodiimide (DIPC) was obtained from Tanabe Chemicals (San Diego, Calif.). 5-dodecanoylaminofluorescein (DAF) and Oregon Green were obtained from Molecular Probes (Eugene, Oreg.). Phosphate-buffered saline (PBS; 1×PBS is 0.01 M phosphate buffered saline containing 0.138 M NaCl and 0.0027 M KCl; pH 7.4), blue dextran, fluorescein, rabbit liver esterase, and paclitaxel were purchased from Sigma (St. Louis, Mo.). N,N-dimethylformamide and tetrahydrofuran (THF) were obtained from Merck (EM Science, Darmstadt, Germany). Dimethylsulfoxide was obtained from Merck and Sigma. These reagents were used without additional purification.

Synthesis procedure: The triblock copolymers were synthesized in a one-pot reaction at 20° C. using in-situ carbodiimide coupling of the PEG and oligo (DTR-SA), as disclosed in Nardin et al., *Langmuir*, vol. 20, 11721-25 (2004), the disclosure of which is incorporated herein by reference. To confirm that this method produced ABA triblock copolymers rather than random block copolymers, a two-step synthesis preparation was also performed in which the oligo (DTO-SA) B-block was prepared by a DIPC and DMPTS-catalyzed reaction of DTO and suberic acid. After being quenched with CTAB and water, this oligomer was isolated by precipitation, purified, and characterized.

In a separate reaction, oligo (DTO-SA) was reacted with monomethoxyterminated PEG (MeO-PEG-OH) under the same coupling conditions.

Block Copolymer Physical Characterization: Molecular weights ($M_n$ and $M_w$) were determined by gel permeation chromatography, GPC (PL-gel columns, pore size $10^5$ and $10^4$ Å, Perkin-Elmer, Shelton, Conn.; Waters 410 RI detector) with 1 mL/min THF flow rate and polystyrene standards. $^1$H Nuclear Magnetic Resonance (NMR) spectra were obtained in $CDCl_3$ at 400 MHz (Varian Unity 400 spectrophotometer, Palo Alto, Calif.): 6.98-7.20 ppm (Ar—H), 5.98 (d, NH), 4.86 (d, CH of tyrosine), 4.08 (m, $OCH_2$ of DTR), 3.65 ($CH_2CH_2$ of PEG), 3.38 (s, $OCH_3$ of PEG), 3.05 (t, $CH_2$ of DT), 2.95 (t, $CH_2$ of SA), 2.56 (m, $CH_2$ of SA; $CH_2$ of DT; $CH_2$ of DT), 1.78 (p, $CH_2$ of SA), 1.60 (p, $CH_2$ of R), 1.50 (p, $CH_2$ of SA), 1.3 (m, $CH_2$ of R) and 0.92 (t, $CH_3$ of R).

Solution differential scanning calorimetry, DSC (DSC-7 calorimeter, Perkin-Elmer, Shelton, Conn.) was performed with a heating/cooling rate of 2° C./min. Solid DSC(2920 modulated differential scanning calorimeter, TA Instruments-Water LLC, New Castle, Del.) was performed as described in d'Acunzo et al., *Macromolecules*, vol. 35, 9366-71 (2002), the contents of which are incorporated herein by reference.

Figure 2:
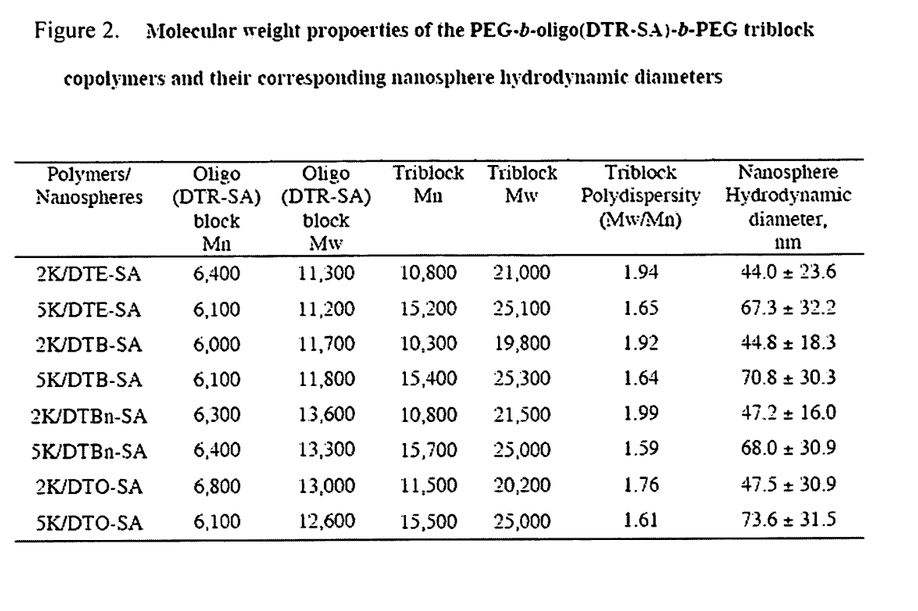
FIG. 2 is a table displaying the molecular weight properties of the PEG-b-oligo(DTR-SA)-b-PEG triblock copolymers and their corresponding nanosphere hydrodynamic diameter.

The molecular weights of the (DTR-SA) blocks, obtained by sampling the one-step reaction mixtures prior to PEG addition, and the molecular weights of the final PEG-b-oligo (DTR-SA)-b-PEG triblocks made in the one-pot process are summarized in FIG. 2 along with the hydrodynamic diameters of the nanospheres that they produce. The $M_n$ values for the 2K PEG-containing triblocks fall within a narrow range between 10,300 and 11,500 g/mol. The $M_n$ values for the 5K PEG-containing triblocks fall within a narrow range between 15,200 and 15,700 g/mol. These results are consistent with the difference in the copolymer molecular weights being dependent upon the PEG blocks in each triblock copolymers. In addition, $^1$H NMR studies support the accuracy of the molecular weights determined by GPC. The ratios of integrated peak areas for DTR-SA and PEG blocks provide the number of (DTR-SA) repeat units in the triblocks (data not shown), and using the known DTR-SA monomer and PEG molecular weights, give copolymers molecular weights that are in close agreement with the GPC molecular weights values.

The molecular weights for the 5K/DTO-SA triblock prepared by the two-step reaction process are $M_n$=15300 g/mol and $M_w$=25300 g/mol. The NMR spectra for the 5K/DTO-SA triblock products prepared by one-step and two-step procedures are identical. Similar comparisons of the other triblocks (not shown) consistently demonstrate the equivalence of the products by the one and two-step reactions.

Figure 3:
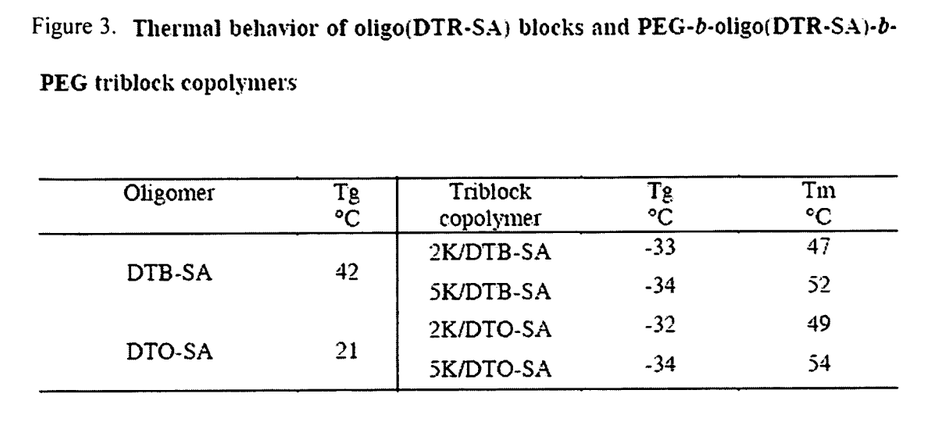
FIG. 3 is a table displaying the thermal behavior of oligo (DTR-SA) blocks and PEG-b-oligo (DTR-SA)-b-PEG triblock copolymers.

The glass transition temperatures, $T_g$, of the hydrophobic oligo(DTR-SA) blocks are all greater than 0° C. and decrease as the lengths of the pendent R groups increase (FIG. 3). Increasing the molecular weight of pure PEG homopolymer from 2000 to 5000 g/mol increases the melting point, $T_m$, from 53° C. to 63° C. In the triblock copolymers 2K/DTO-SA and 5K/DTO-SA, the increase in PEG molecular weights from 2000 to 5000 g/mol causes a similar increase in $T_m$ from 49° C. to 54° C. In all cases, the melting points of the copolymers are lower than the melting points of the corresponding pure PEG blocks, suggesting that the DTR-SA units reduces the degree of PEG crystallinity. Similarly, the difference between the $T_g$ values of −33° C. for all the triblocks and that of PEG homopolymer (−40° C.) can be attributed to a mixed phase morphology in the triblocks.

Nanosphere Preparation: Self-assembly of the copolymers into nanospheres was induced by drop-wise addition of 100 mg/mL triblock oligomer in THF solution into deionized water under mild agitation to a final oligomer concentration of 4 mg/mL. The resulting turbid aqueous dispersions were filtered sequentially through 0.45 μm, 0.22 μm and 0.1 μm size PVDF syringe filters (Millipore, Bedford, Mass.) and the clear filtrates were used for all physical characterizations. The hydrodynamic diameters of the nanospheres were determined by dynamic light scattering (PSS Nicomp Particle Sizing Systems, Santa Barbara, Calif.) at 30° C. using cumulant analysis and the Stokes-Einstein equation, and were consistent with particles sizes measured by electron microscopy as disclosed in Nardin et al., *Langmuir*, vol. 20, 11721-25 (2004).

Purified nanospheres were isolated by ultracentrifugation of 12.25 mL nanosphere solutions at 65,000 rpm (290,000×g) for 2.5 hours at 25° C. (Beckman L8-70M ultracentrifuge, Beckman Coulter, Fullerton, Calif.). Following removal of the supernatant, the pelleted nanospheres were washed twice with water and resuspended with gentle agitation in 1 mL of water at 25° C. The volume of the resuspended pellets was then increased to 12.25 mL by the addition of water and the solutions were filter sterilized.

Nanosphere Characterization: All of the triblock copolymers described here self-assemble spontaneously into nanospheres when added slowly to aqueous solution. The hydrodynamic diameters of the nanospheres fall into two groups of about 46 nm and 70 nm, depending upon whether they contain 2K or 5K PEG blocks, respectively, and not upon the particular pendent R groups. The size distributions of 5K/DTO-SA nanospheres before and after ultracentrifugation are 62.9±31.3 nm and 60.6±25.9 nm, respectively, indicating that neither the presence of residual co-solvent in the nanosphere preparation nor ultracentrifugation have a significant effect on nanosphere structures. Since the nanosphere self-assembly is driven by non-covalent interactions, the nanospheres disintegrate upon dilution below the critical aggregation concentration (CAC). However, the CAC of 0.26 µg/mL for 2K/DTO-SA triblock is significantly lower than previously published values for other self-assembling block oligomer systems.

The $T_g$'s of the nanospheres are 21° C. for all nanosphere compositions as determined by solution DSC. The presence of the hydrated PEG blocks appears to plasticize the glass transition of the hydrophobic DTR-SA core components, whose $T_g$'s are 21° C. or higher.

This family of triblock copolymers is designed to degrade into biocompatible compounds under physiological conditions. HPLC analysis reveals approximately 70% of DTE monomer (FIG. 1, R=ethyl ester) is converted to the free acid, desaminotryosine (DT) following incubation in the presence of rabbit liver esterase for 30 min. The 5K/DTO-SA nanospheres appear stable when incubated in PBS at pH 7.4 and 37° C. for up to 6 months, when a white precipitate forms and filtration results in the loss of all structures detectable by DLS.

Example 3

Nanosphere-Model Compound Interactions

Nanosphere complexes with model compounds were prepared by combining 20 mg of triblock copolymer with either 100 µg of fluorescent dye in 200 µL of DMF or with 200 µg of paclitaxel in 200 µL of DMF containing 1% DMSO. These solutions were added dropwise to 4.8 mL of deionized water with constant stirring, the resulting nanosphere-solute complexes were filtered (0.22 µm pore-sized) and stored in glass or polypropylene containers at room temperature prior to use. For specific applications, this procedure was scaled up threefold. Free solute solutions were prepared in this same manner except that the triblocks were absent.

Size exclusion chromatography (SEC) of nanosphere-solute complexes was performed using Sepharose CL-4B (Amersham Biosciences, Piscataway, N.J.) and PBS as mobile phase. The bottom frit for the column was porous polytetrafluoroethylene (Small Parts, Inc., Miami Lakes, Fla.), which significantly reduced the binding of hydrophobic molecules emerging from the column. In general, 36×0.25 mL fractions were collected. The column void volume was determined using high molecular weight fluorescently labeled dextran. Nanospheres were detected by their UV absorbance (260 nm; PowerWave, Bio-Tek Instruments, Inc., Winooski, Vt.) and fluorescent dyes were detected by their fluorescence (excitation, 485 nm/emission, 538 nm; Spectra Max Gemini, Molecular Devices, Sunnyvale, Calif.). When necessary, in order to eliminate nanosphere-dependent quenching, 50 µL of each fraction were combined with 150 µL of DMF/PBS (1:1) prior to fluorescence determination.

Paclitaxel concentrations in nanosphere complexes were determined by high performance liquid chromatography, HPLC (3 cm C18 HPLC column, Perkin-Elmer, Shelton, Conn.) with a gradient of 0.1% water/acetonitrile/trifluoroacetic acid as the mobile phase. Nanosphere-paclitaxel complexes were prepared by combining 60 mg triblock oligomer with 600 µg paclitaxel in 600 µL DMF with 1% DMSO, and adding this dropwise to 14.4 mL water. Free paclitaxel was separated from paclitaxel-containing nanospheres by ultracentrifugation as described above. Then, 1.5 mL of resuspended paclitaxel-nanosphere suspension was freeze-dried and redissolved in 0.15 mL of methylene chloride and 0.1 mL of acetonitrile under vigorous vortexing. Methylene chloride was evaporated under a stream of nitrogen and an aliquot of each final clear solution was analyzed by HPLC; paclitaxel was detected by absorbance at 230 nm. The area of each eluted peak was quantified by comparison with free paclitaxel standards in acetonitrile. Drug binding efficiency is expressed as mg of the paclitaxel per g copolymer in a given paclitaxel-nanosphere complex.

Cytotoxicity Assays: For cytotoxicity assays of the nanospheres in the absence of associated drug molecules, KB cervical carcinoma cells (500 to 5000 cells) were plated in a 96-well plate in a total of 100 µL of DMEM (Sigma) containing 10% fetal bovine serum, FBS. Approximately 1 to 2 hours later, 10 µL of nanosphere solution was added to the cells and the cells were grown at 37° C./5% $CO_2$ for 8 to 72 hours. Cell number was determined indirectly by an MTS assay following conditions described by the manufacturer (CellTiter 96 Aqueous One Solution Cell Proliferation Assay; Promega Corp., Madison, Wis.). The KB cell line was obtained from the American Type Culture Collection (CCL-17; Manassas, Va.) and stocks were maintained at 37° C./5% CO2 in folate-free RPMI 1640 media (Grand Island, N.Y.) in the presence of 10% heat-inactivated FBS and penicillin/streptomycin.

To determine paclitaxel activity, 5K/DTO-SA nanospheres were prepared in the presence of paclitaxel and pelleted by ultracentrifugation as described above. Supernatants were recovered and nanosphere pellets were washed and resuspended into the original starting volume. Serial dilutions of the initial preparation (prior to centrifugation), the recovered supernatant, and the resuspended nanosphere pellet were prepared and 10 µL of each was applied to KB cells. Following 3 days of growth, the volume required for 50% growth inhibition was determined.

Figure 4:
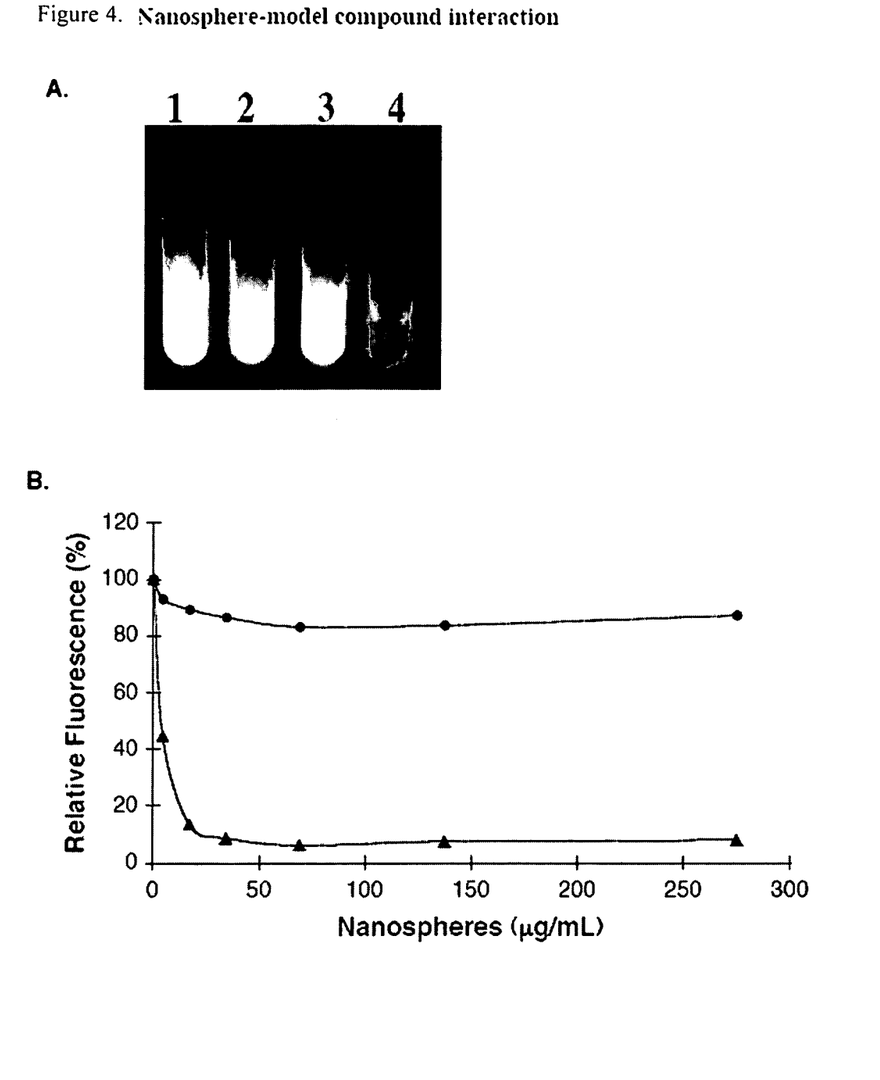
FIG. 4A demonstrates fluorescence in the presence or absence of 5K/DTO-SA nanospheres as follows: (1) free fluorescein; (2) nanospheres/fluorescein; (3) free DAF; (4) nanospheres/DAF.
FIG. 4B is a graph showing relative fluorescence as a function of nanosphere concentration wherein ultracentrifuge-purified 5K/DTO-SA nanospheres were added to a 2.5 µM solution of DAF (▲) or a 1 µM solution of fluorescein (●) in 0.25% DMF.

Nanosphere Interaction with Fluorescent Model Compounds: All of the nanospheres quench the fluorescence of the hydrophobic dye, DAF, but have little effect on the hydrophilic dye, fluorescein (FIG. 4B). At a nanosphere concentration of 25 µg/mL and a ratio of approximately 2 moles DAF/mole oligomer, the fluorescence of DAF is reduced by almost an order of magnitude. In contrast, even at a ratio of 1 mole fluorescein/mole oligomer, the fluorescence is only reduced by 15%. These nanosphere-dependent effects on DAF fluorescence are indicative of a physical complexation of DAF molecules by the nanospheres. In the absence of nanospheres, the average fluorescence by DAF and fluorescein, were 4200 and 8300 units, respectively.

Figure 5:
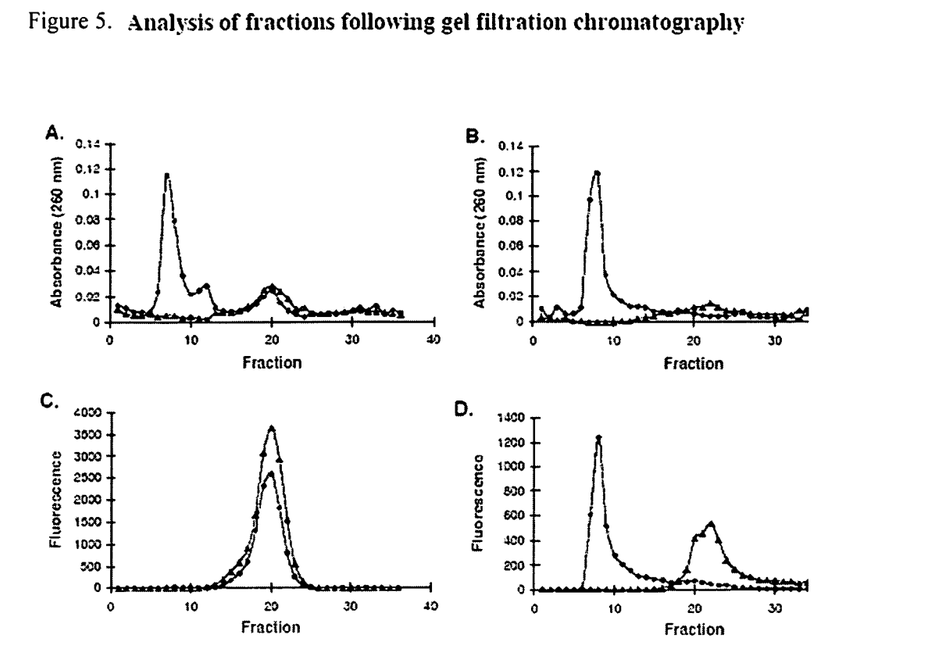
FIG. 5A shows the detection of nanospheres following fractionation of free fluorescein (▲) and nanospheres prepared in the presence of fluorescein (●)
FIG. 5B shows the detection of nanospheres following fractionation of free DAF (▲) and nanospheres prepared in the presence 19 of DAF (●)
FIG. 5C shows the detection of fluorescein following fractionation of free fluorescein (▲) and nanospheres prepared in the presence of fluorescein (●)
FIG. 5D shows the detection of DAF following fractionation of free DAF (▲) and nanospheres prepared in the presence of DAF (●)
Figure 6:
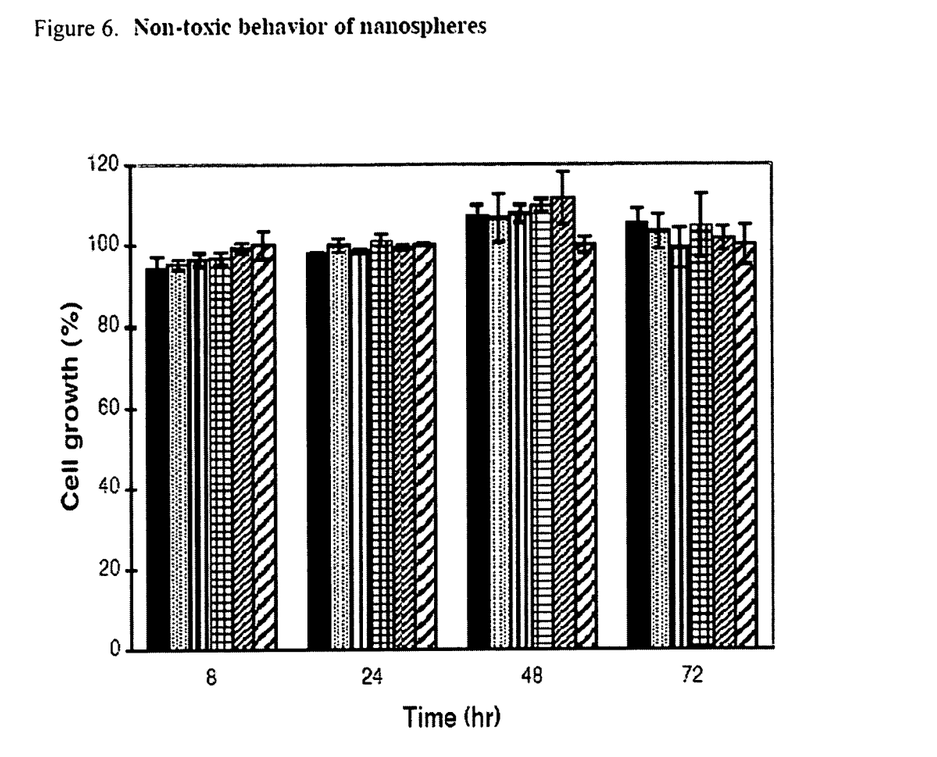
FIG. 6 is a graph displaying the effect of 5K/DTO-SA nanospheres on KB cells incubated in the presence of nanospheres at 4 mg/mL (▣), 2 mg/mL (◐), 1 mg/mL (◨), 0.5 mg/mL (▤), 0.1 mg/mL (▨) or 0 mg/mL (▱) for 8 to 72 hr, and results are presented as a percentage of cell growth in the absence of nanospheres.
Figure 7:
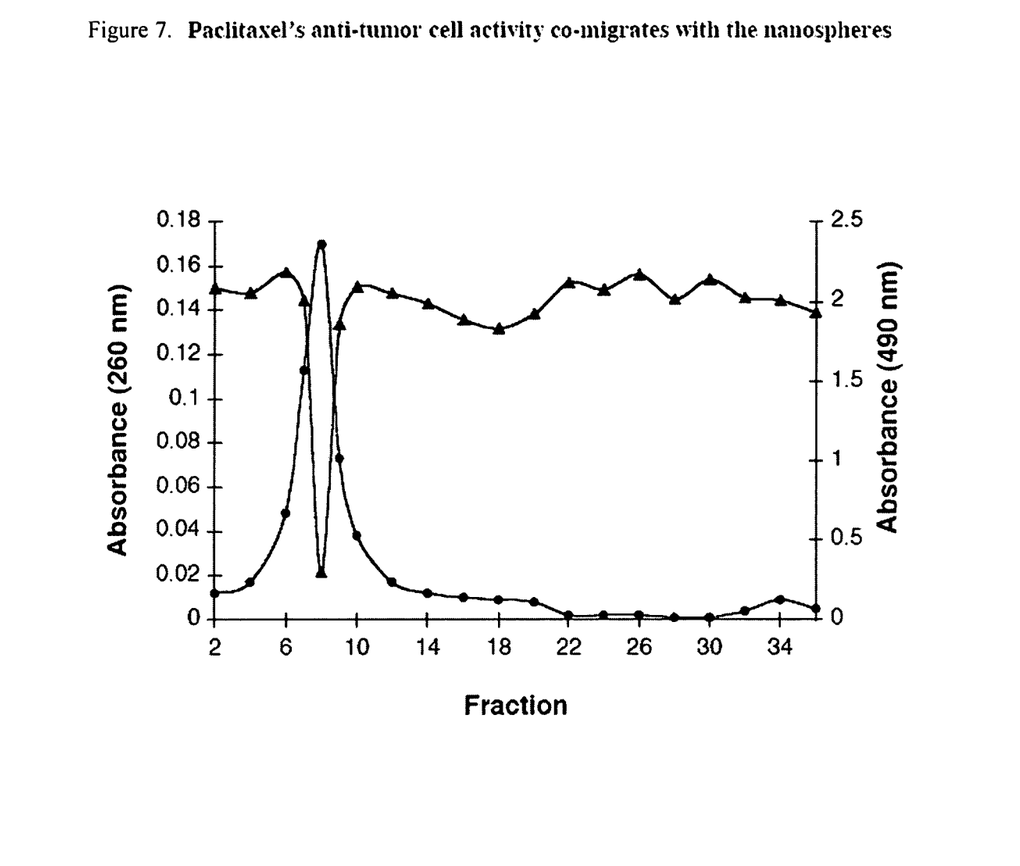
FIG. 7 is a graph displaying absorbance as a function of gel filtration chromatography fraction in which even numbered fractions and fractions 7 and 9 of 5K/DTOSA nanospheres formed in the presence of paclitaxel and fractionated by gel filtration chromatography were detected by absorbance at 260 nm (●), paclitaxel activity was determined as a function of KB cell growth using 20 µL of each fraction, and cell growth was determined using an MTS assay and was measured at 490 nm (▲).

Strong binding of DAF by the nanospheres is also evident from the co-migration of DAF and nanospheres in SEC experiments (FIG. 5). The nanospheres emerge in the void volume, fractions 7 and 8, regardless of the presence (FIGS. 5A and 5B) or absence (data not shown) of dyes. In the absence of nanospheres, DAF and fluorescein emerge at fractions 20 and 22, respectively (FIGS. 5C and 5D). The peak fluorescence is also at fraction 20 for nanospheres formed in the presence of fluorescein (FIG. 5C) and another hydrophilic fluorescent dye, Oregon Green (data not shown). These results indicate a lack of significant complex formation between the nanospheres and hydrophilic molecules. In contrast, the peak fluorescence occurs at fractions 7 and 8 (FIG. 5D) for nanospheres formed in the presence of DAF. 5K/DTOSA nanospheres were detected by absorbance at 260 and fluorescein and DAF were detected by fluorescence. To avoid nanosphere-dependent quenching, all fluorescent readings were performed in the presence of DMF/PBS as described above.

Using ultracentrifugation to separate nanosphere-bound dye from free dye, the fraction of DAF molecules that strongly associate with the 5K/DTO-SA nanospheres is found to be approximately 95% (4.75 mg/g oligomer), based upon fluorescent analysis of the nanosphere/DAF preparation prior to ultracentrifugation, and the supernatant and the resuspended nanosphere pellet recovered after centrifugation. Only 1% of the DAF remains in the supernatant. The remaining 4% of DAF molecules are probably weakly associated with the nanoparticles and are removed during the wash. When DAF is added to pre-formed nanospheres and subjected to ultracentrifugation, 95%, and 3% of the input DAF are recovered in the pellet and supernatant, respectively. Thus, the nanospheres act as an effective sink for absorbing and binding hydrophobic molecules. When DAF containing nanospheres are dialyzed against water, an initial loss of about 30% of the total DAF concentration (determined by fluorescence) is observed in the first 24 hrs, followed by minimal loss of dye over the next 4 days. Thus, the nanospheres act as an effective sink for absorbing and binding hydrophobic molecules.

Nanosphere Interactions with Paclitaxel: In preliminary studies of the effects of oligomer hydrophobicity on paclitaxel binding by nanospheres, the concentration of paclitaxel bound to the nanospheres after filtration and ultracentrifugation is found by HPLC analyses to be 3.5 mg paclitaxel/g oligomer for both 5K/DTO-SA and 2K/DTOSA. For the less hydrophobic ethyl pendent ester oligomers, 5K/DTE-SA and 2K/DTESA, the amount of paclitaxel bound to the nanospheres is 3.2 mg/g oligomer. These results illustrate the "tunable" nature of this oligomeric system.

Cytotoxicity of Nanospheres and Paclitaxel-Nanosphere Complexes: No short-term cytotoxic effects or changes in viability of KB cells are observed when the cells are exposed in vitro to ultracentrifuge-purified 5K/DTO-SA nanospheres at concentrations ranging from 0.1 mg/mL to 4 mg/mL (FIG. 6). In addition, no cytotoxic effects are observed in KB cells exposed to nanospheres of 5K/DTE-SA, 5K/DTB-SA, or 5K/DTBn-SA at 1 mg/ML for 72 hours (data not shown). These results are consistent with preliminary short-term cytotoxicity tests performed previously with 2K/DTO-SA nanospheres.

Growth inhibition of KB human carcinoma cells by paclitaxel is found to co-fractionate with 5K/DTO-SA nanospheres in SEC experiments (FIG. 7). KB cell growth inhibition, which is quantified here by the viable cell population measured in the MTS assay by absorbance measurements at 490 nm, occurs in direct proportion to the amount of paclitaxel-nanosphere complex that is present in a given column fraction. The peak killing efficacy occurs in precisely the same fraction as the peak elution concentration (fraction 8) of paclitaxel-nanosphere complex. In addition, the relative activity for 50% growth inhibition of KB cells by paclitaxel-nanosphere complexes after ultracentrifugation is 40% of the initial preparation's activity, as determined by titrating the KB cells with aliquots of the initial preparation and resuspended pellets (data not shown). By the same means, the relative activity of the supernatant is found to be 9% of the initial preparation's activity. These activities are consistent with the concentrations obtained by HPLC for paclitaxel binding to the nanospheres and reflect the fact that paclitaxel is sparingly soluble in aqueous solutions. The LC50 of 5K/DTO-SA-paclitaxel and free paclitaxel for KB cell growth inhibition are found to be 2.2±0.3 nM and 2.9±1.1 nM, respectively. Thus the nanospheres do not inhibit the activity of the complexed paclitaxel. Nanospheres prepared in the absence of drug and fractionated in an identical manner did not inhibit KB cell growth (data not shown).

Example 4

Preparation of poly(ethylene glycol)-block-oligo-(DTO carbonate)-block-poly(ethylene glycol) Self-Assembling Nanospheres Chemicals: Desaminotyrosyl tyrosine octyl ester (DTO) was prepared using known procedures. Methylene chloride (DCM) (HPLC grade) and pyridine (certified ACS) were purchased from Fisher Scientific, (Pittsburgh, Pa.). Triphosgene (TP) was purchased from Aldrich Chemical Co. (Milwaukee, Wis.). Poly(ethylene glycol) (PEG) (Mw=5000) was purchased from Fluka (Switzerland). These reagents were used without additional purification.

Synthesis procedure: A 0.5 L 3-necked flask equipped with a mechanical stirrer and pump was purged with $N_2$ for 15 min. PEG was added to the flask followed by TP (solid) and DCM. The mixture was stirred to obtain a clear solution (10-15 min). At this point, reaction mixture contains "activated PEG"—PEG-chloroformate and an excess of unreacted TP. DTO and DCM were placed in the bottle with screw cap, and the TP solution was added to the reaction mixture using FMI pump (over 1 h). After the addition was complete, 10 ml of DCM were added to the bottle and were added to the reaction mixture over 10 min using the pump. After addition was complete, a 150 mL aliquot was withdrawn, evaporated to dryness with air and diluted with 1 mL of THF, filtered, and the filtrate was analyzed by GPC to determine the molecular weight distribution. GPC chromatogram revealed a mixture of products and reacted monomers. After the GPC run was completed, addition of 100 mL $H_2O$ quenched the reaction.

Work-up: The entire reaction mixture was concentrated by evaporation to a thick syrup (ca. 10 mL total), which was then precipitated with 60 mL of 2-propanol (drop-wise addition) and allowed to settle. The product was obtained as yellow thick oil, and the solvents were decanted off. The precipitate was dried (under $N_2$) for 20 min, redissolved in 10 mL of methylene chloride and precipitated with 60 mL of 2-propanol. Step 3 was repeated 2 more times with: a) 50 mL of methanol:IPA=1:1; b) 50 mL methanol. The product (thick gum) was dried under a stream of nitrogen followed by vacuum drying.

Block Copolymer Physical Characterization: The molecular weight of PEG5K-oligo DTO carbonate-PEG5K was determined to be Mn=39,102 and Mw=53,758 by gel permeation chromatography, GPC (PL-gel columns, pore size $10^5$ and $10^4$ Å, Perkin-Elmer, Shelton, Conn.; Waters 410 RI detector) with 1 mL/min THF flow rate and polystyrene standards. $^1$H Nuclear Magnetic Resonance (NMR) spectra were obtained in DMSO at 400 MHz (Varian Unity 400 spectrophotometer, Palo Alto, Calif.) and indicated about 180 (DTO-carbonate) units relative to PEG, which was in agreement with the PEG5K-oligo DTO carbonate-PEG5K structure.

Nanosphere Preparation and Characterization: Self-assembly of the oligomers into nanospheres was induced by drop-wise addition of 100 mg/mL triblock oligomer in THF solution into deionized water under mild agitation to a final oligomer concentration of 4 mg/mL. The resulting turbid aqueous dispersions were filtered sequentially through 0.45 μm, 0.22 μm and 0.1 μm size PVDF syringe filters (Millipore, Bedford, Mass.) and the clear filtrates were used for all physical characterizations. The hydrodynamic diameters of the nanospheres were determined by dynamic light scattering (PSS Nicomp Particle Sizing Systems, Santa Barbara, Calif.) at 30° C. using cumulative analysis and the Stokes-Einstein equation, which yielded the following results after filtration: 0.45 μm: 132.4±48.6 nm; 0.22 μm: 121.5±39.0 nm; and 0.1 μm: 111.9±32.0 nm. All of the triblock oligomers described here self-assemble spontaneously into nanospheres when added slowly to aqueous solution. The hydrodynamic diameter of the nanospheres is about 112 nm.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A composition comprising (a) vesicular nano spheres of a triblock oligomer consisting of a single A-B-A structure wherein each A end block is a poly(alkylene oxide) having the structure:

and the B middle block is hydrophobic with the same or different repeating units having the structure according to Formula II:

wherein X is

Z is an integer, between 2 and about 100, inclusive, that provides a middle block with a weight-average molecular weight between about 1000 and about 25,000 g/mol; $R_1$ is CH=CH or $(CH_2)_n$ wherein n is from 0 to 18, inclusive; $R_2$ is selected from the group consisting of hydrogen and straight and branched alkyl and alkylaryl groups containing up to 18 carbon atoms; and R is selected from the group consisting of a bond or straight and branched alkyl and alkylaryl groups containing up to 18 carbon atoms; and (b) a hydrophobic compound complexed by said nanospheres;

wherein m for each A is independently selected to provide a molecular weight for each A between about 1000 and about 15,000 g/mol; $R_3$ for each A and within each A is independently selected from the group consisting of hydrogen and lower alkyl groups containing from one to four carbon atoms; and a is an integer greater than or equal to one; and wherein said triblock oligomer is fully resorbable and degrades by hydrolysis in vivo into biocompatible and non-cytotoxic degradation products.

2. The composition of claim 1, wherein said end blocks have the structure $CH_3O$—$[CH_2$—$CH_2$—$O$—$]_m$.

3. The composition of claim 1, wherein Z is about 10.

4. The composition of claim 1, wherein one or more of R, $R_1$, and $R_2$ contain an ether linkage.

5. The composition of claim 1, wherein $R_1$ is —$CH_2$—$CH_2$—.

6. The composition of claim 1, wherein $R_2$ is selected from the group consisting of ethyl, butyl, hexyl, octyl, decyl, dodecyl and benzyl groups.

7. The composition of claim 1, wherein R contains up to 12 carbon atoms.

8. The composition of claim 7, wherein R is selected from the group consisting of —$CH_2$—$CH_2$—$C(=O)$—, —$CH=CH$—, —$CH_2$—$CH(-OH)$—, —$CH_2$—$C(=O)$— and (—$CH_2$—)$_z$, wherein z is between 0 and 12, inclusive.

9. The composition of claim 1, wherein the complexed hydrophobic compound is a biologically or pharmaceutically active compound.

10. A composition for delivering a hydrophobic compound to a patient in need thereof comprising a pharmaceutically acceptable carrier and an effective amount of the composition of claim 1.

11. The composition of claim 10, wherein said nanospheres are embedded or dispersed in a drug delivery oligomer matrix.

12. The composition of claim 9, 10, or 11, wherein said active hydrophobic compound is selected from the group consisting of anti-tumor agents, antibiotics, antimicrobials, statins, peptides, proteins, hormones, and vaccines.

13. The composition of claim 12, wherein said active hydrophobic compound is selected from the group consisting of paclitaxel, camptothecin, 9-nitrocamptothecin, cisplatin, carboplatin, ciprofloxacin, doxorubicin, rolipram, simvastatin, methotrexate, indomethacin, probifopen, ketoprofen, iroxicam, diclofenac, cyclosporine, etraconazole, rapamycin, nocodazole, colchicine, ketoconazole, tetracycline, minocycline, doxycycline, ofloxacin, gentamicin, octreotide, calcitonin, interferon, testosterone, progesterone, estradiol, estrogen, and insulin.

14. The composition of claim 10, wherein the complexed compound is a contrast agent.

15. A method for site-specific or systemic drug delivery comprising administering to a patient in need thereof the composition of claim 10 or 11.

* * * * *